United States Patent
Sridhar et al.

(10) Patent No.: US 6,671,632 B2
(45) Date of Patent: Dec. 30, 2003

(54) METHODS AND APPARATUS FOR DETERMINING RESILIENCE OF SPRING WASHERS

(75) Inventors: Bettadapur Narayanarao Sridhar, Cupertino, CA (US); John Joseph Lynch, Gilroy, CA (US); Maharaj Krishen Kaul, Fremont, CA (US)

(73) Assignee: General Electric Company, Schenectady, NY (US)

( * ) Notice: Subject to any disclaimer, the term of this patent is extended or adjusted under 35 U.S.C. 154(b) by 39 days.

(21) Appl. No.: 10/146,591

(22) Filed: May 14, 2002

(65) Prior Publication Data

US 2003/0216872 A1 Nov. 20, 2003

(51) Int. Cl.[7] .............................................. G06F 19/00
(52) U.S. Cl. ....................................................... 702/33
(58) Field of Search .............................. 702/31, 33, 32, 702/55, 95, 116; 703/7, 1; 73/729.1, 286, 40, 862.23, 649, 40.5 A, 862.541, 862.21; 700/18, 109; 401/111; 324/421; 604/246; 600/561; 177/25, 13; 209/538

(56) References Cited

U.S. PATENT DOCUMENTS

| | | | | | |
|---|---|---|---|---|---|
| 4,754,417 A | * | 6/1988 | Beeson et al. | .................. | 703/7 |
| 5,624,409 A | * | 4/1997 | Seale | .......................... | 604/246 |
| 6,062,756 A | * | 5/2000 | Sasaki | ......................... | 401/111 |
| 6,313,636 B1 | * | 11/2001 | Pohl et al. | .................. | 324/421 |

OTHER PUBLICATIONS

"The Uniform–Section Disk Spring" by J. O. Almen and A. Laszlo, published by the American Society of Mechanical Engineers in May 1936, vol. 58, No. 4.

* cited by examiner

Primary Examiner—John Barlow
Assistant Examiner—Xiuqin Sun
(74) Attorney, Agent, or Firm—Armstrong Teasdale LLP (57) ABSTRACT

A method enables the resilience of a plurality of spring washers stacked in a series arrangement to be determined. The method comprises determining the potential energy for the series arrangement by integrating the product of the axial load applied to the series arrangement, the displacement of the series arrangement, and the number of spring washers stacked in the series arrangement, and solving at least two non-linear equations to determine the resilience of the spring washers stacked in the series arrangement.

17 Claims, 5 Drawing Sheets

METHODS AND APPARATUS FOR DETERMINING RESILIENCE OF SPRING WASHERS

BACKGROUND OF THE INVENTION

This invention relates generally to spring washers and more particularly, to methods and apparatus for determining resilience of spring washers.

Conical spring washers are often used in fastening systems or support systems to insure that a compressive force is maintained on the clamped members throughout an intended service cycle. Once compressed, the conical spring washer continuously produces a force exerted on its immediately adjoining members (a separating force). When a conical spring washer is compressed between a bolt head or nut securing a clamped member and the clamped member, the separating force of the conical spring washer assists in clamping the clamped member. The spring washer's effective operating travel produces and maintains a force on clamped members when there is differential movement (strain) between and among the clamped members and the clamping member, e.g., a bolt.

Spring washers are also used in applications to facilitate limiting an amount of movement of a component when the component experiences a failure or potentially failing event. For example, within a reactor pressure vessel (RPV) of a boiling water reactor (BWR), housing support rods below the RPV are contained within control rod housing supports that are coupled to the RPV using a plurality of spring washers and a nut. More specifically, the spring washers are positioned at the top end of the hanger support rods to facilitate limiting an amount of downward travel of the housing support rods in the event of a failure of the control rod drive housing.

Spring washers are typically used in such applications because the coned, annular-disk washers provide load-deflection characteristics that may not be readily obtainable with more conventional forms of springs. Accordingly, such washers are variably selected based on the number, arrangement, and characteristics of the spring washers used in such applications, and to facilitate optimizing each spring within an application, at least some known design formulas are used to determine suitable spring geometry characteristics. However, known formulas provide only limited characteristic accuracy because only known formulas only determine characteristics of one spring washer at a time. As such, to determine the characteristics of a stack of washers arranged in a series and/or parallel arrangement, numerous approximations must be made. Accordingly, spring characteristics based on such approximations may be inaccurate and may lead to failure of associated components.

BRIEF SUMMARY OF THE INVENTION

In one aspect, a method for determining resilience of a plurality of spring washers stacked in a series arrangement is provided. The method comprises determining the potential energy for the series arrangement by integrating the product of the axial load applied to the series arrangement, the displacement of the series arrangement, and the number of spring washers stacked in the series arrangement, and solving at least two non-linear equations to determine the resilience of the spring washers stacked in the series arrangement.

In another aspect, an apparatus is provided for determining resilience of a plurality of spring washers stacked in a series arrangement. The apparatus includes a processor programmed to integrate the product of the axial load applied to the series arrangement, the displacement of the series arrangement, and the number of spring washers stacked in the series arrangement to determine the potential energy for the series arrangement, and solve at least two non-linear equations to determine the resilience of the spring washers stacked in the series arrangement.

In a further aspect of the invention, a system for determining resilience of a plurality of spring washers stacked in a series arrangement is provided. The system includes a client system including a browser, a data storage device for storing information relevant to a plurality of users, and a server system configured to be coupled to the client system and the data storage device. The server system is further configured to integrate the product of the axial load applied to the series arrangement, the displacement of the series arrangement, and the number of spring washers stacked in the series arrangement to determine the potential energy for the series arrangement, and to solve at least two non-linear equations to determine the resilience of the spring washers stacked in the series arrangement.

DETAILED DESCRIPTION OF THE INVENTION

Systems and methods for determining resilience of spring washers are described herein. The systems and methods are not limited to the specific embodiments described herein. Rather, and in addition, components of each system and each method can be practiced independently and separately from other components and methods described herein. Each component and method can be used in combination with other components and other methods.

Figure 1:
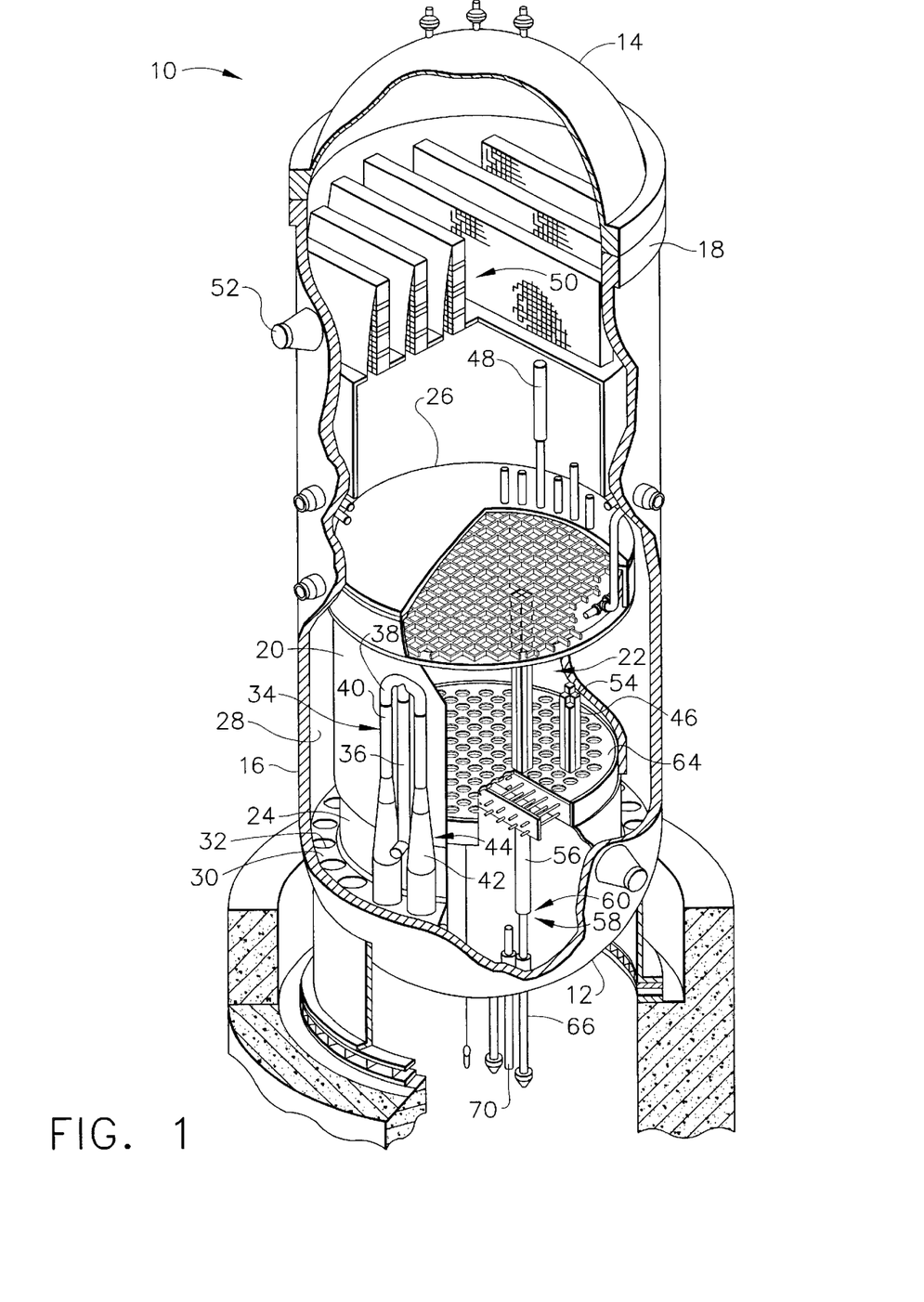
FIG. 1 is a sectional view, with parts cut away, of a boiling water nuclear reactor pressure vessel (RPV)
Figure 2:
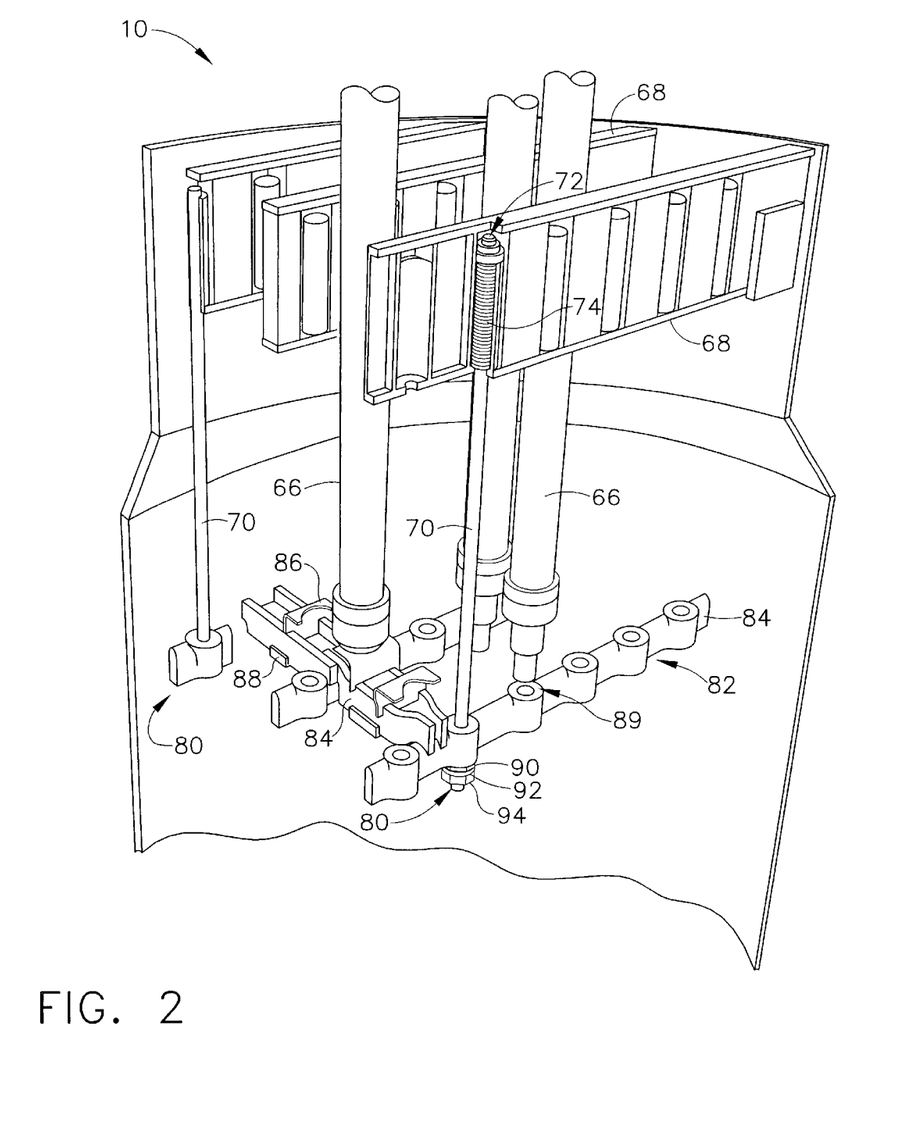
FIG. 2 is an enlarged partial view of an undervessel portion of the RPV shown in FIG. 1.

FIG. 1 is a sectional view, with parts cut away, of a boiling water nuclear reactor pressure vessel (RPV) 10. FIG. 2 is an enlarged partial view of an undervessel portion of RPV 10. RPV 10 has a generally cylindrical shape and is closed at one end by a bottom head 12 and at its other end by a removable top head 14. A side wall 16 extends from bottom head 12 to top head 14. Side wall 16 includes a top flange 18. Top head 14 is attached to top flange 18. A cylindrically shaped core shroud 20 surrounds a reactor core 22. Shroud 20 is supported at one end by a shroud support 24 and includes an opposed removable shroud head 26. An annulus 28 is formed between shroud 20 and side wall 16. A pump deck 30, which has a ring shape, extends between shroud support 24 and RPV side wall 16. Pump deck 30 includes a plurality of circular openings 32, with each opening housing a jet pump 34. Jet pumps 34 are circumferentially distributed around core shroud 20. An inlet riser pipe 36 is coupled to two jet pumps 34 by a transition assembly 38. Each jet pump 34 includes an inlet mixer 40, and a diffuser 42. Inlet riser 36 and two connected jet pumps 34 form a jet pump assembly 44.

Heat is generated within core 22, which includes fuel bundles 46 of fissionable material. Water circulated up through core 22 is at least partially converted to steam. Steam separators 48 separate steam from water, which is recirculated. Steam dryers 50 remove residual water from the steam. The steam exits RPV 10 through a steam outlet 52 near vessel top head 14.

The amount of heat generated in core 22 is regulated by inserting and withdrawing a plurality of control rods 54 of neutron absorbing material, for example, hafnium. To the extent that control rod 54 is inserted adjacent fuel bundle 46, it absorbs neutrons that would otherwise be available to promote the chain reaction which generates heat in core 22.

Each control rod 54 couples with a control rod drive mechanism (CARD) 58 to form a control rod apparatus 60. CARD 58 moves control rod 54 relative to a core support plate 64 and adjacent fuel bundles 46. CARD 58 extends through bottom head 12 and is enclosed in a control rod drive mechanism housing 66. A control rod guide tube 56 extends vertically from the control rod drive mechanism housing 66 to core support plate 64. Control rod guide tubes 56 restrict non-vertical motion of control rods 54 during control rod 54 insertion and withdrawal. Control rod guide tubes 56 can have any number of shapes, for example a cruciform shape, a cylindrical shape, a rectangular shape, a Y-shape, and any other suitable polygonal shape.

In FIG. 2, horizontal beams 64 are coupled immediately below RPV bottom head 12 between rows of CRD housings 66. A plurality of hanger rods 70 are coupled to beams 68. In one embodiment, vessel 10 includes four hanger rods 70. More specifically, a first end 72 of each hanger rod 70 is supported from beam 68 by a plurality of disc springs 74. A second end 80 of each hanger rod 70 is coupled to a control rod drive housing support 82. Housing support 82 includes a plurality of substantially parallel support bars 84 coupled together by a plurality of grid plates 86 and grid clamps 88.

More specifically, bars 84 extend between adjacent CRD housings 66 and are positioned such that a gap 89 is defined between housing support 82 and CRD housings 66. Gap 89 facilitates preventing vertical contact stresses caused by thermal expansion between housing support 82 and CRD housings 66 during plant operation.

As an operating temperature increases, gap 89 decreases, however, during normal operating conditions, gap 89 remains defined between housing support 82 and housings 66. Each hanger rod second end 80 is coupled to a respective support bar 84 by a nut 90, a jam nut 92, and a plurality of washers 94 extending therebetween. In a postulated CRD housing 66 failure, CRD housing support 82 is considered loaded when CRD housing 66 contacts housing support 82. The resulting load is then carried by grid plates 86, support bars 84, hanger rods 70, disc springs 74, and adjacent beams 68. As a result, disc springs 74 and washers 94 facilitate limiting an amount of downward travel of CRD housing support 82 in the event of a failure of CRD housing 66.

Figure 3:
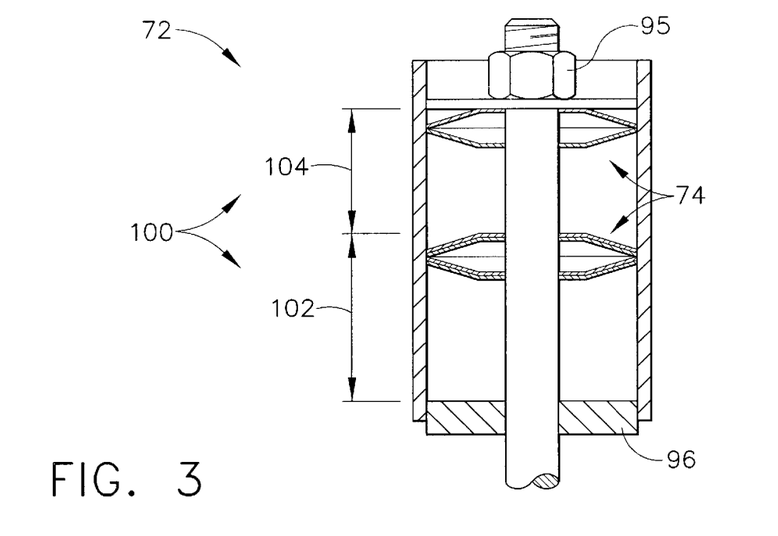
FIG. 3 is an enlarged schematic view of a hanger rod used with the RPV shown in FIG. 2.
Figure 4:
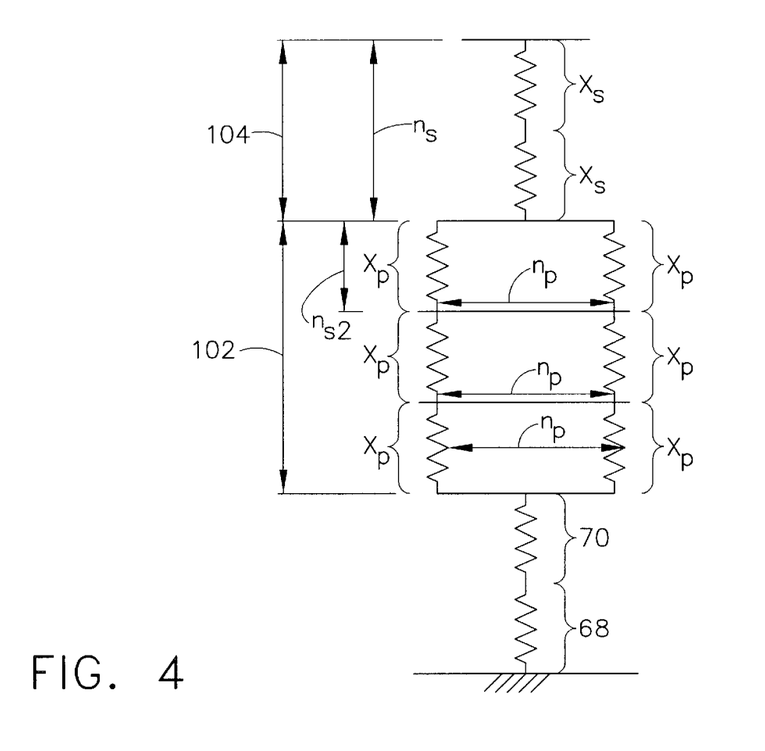
FIG. 4 is a schematic diagram of a partial washer stack used with the hanger rod shown in FIG. 3.

FIG. 3 is an enlarged schematic view of hanger rod first end 72. FIG. 4 is a schematic diagram of washers 74 used with hanger rod first end 72. Washers 74 are spring washers, also known as coned-disk springs, and are used to maintain a constant force regardless of dimensional variations due to wear. In one embodiment, washers 74 are Belleville washers. A plurality of washers 74 are typically stacked together between a jam nut 95 and a nut 96 to form a stack 100. Because of the conical shape of washers 74, washers 74 may be stacked in a parallel stack 102 or in a series stack 104. Within a parallel stack 102, all washers 74 are stacked in the same direction in pairs, and in contrast, in a series stack 104, washers 74 are stacked in alternating singles such that a convex surface of each washer 74 is against a concave surface of an adjacent washer 74.

Each hanger support rod 70 includes a parallel stack 102 and a series stack 104 (an arrangement known as a combination stack). At least two washers 74 are included within each stack 102 and 104, and stacks 102 and 104 are arranged such that stack 102 is above stack 104. In the exemplary embodiment, series stack 104 includes ten washers 74, and parallel stack 102 includes fourteen pairs of washers 74. More specifically, the number $n_s$ of washers 74 within series stack 104 and the number $n_p$ of washers 74 within parallel sets 102 are variably selected.

As a load P is applied to contacts housing support 82 (shown in FIG. 2), each washer 74 within series stack 104 deflects $X_s$ and each washer within parallel stack 102 deflects $X_p$ for a total stack deflection $X_{tOt}$. In addition, as load P is applied, hanger rod 70 and a respective beam 68 each function as linear springs and as such are graphically depicted within FIG. 4.

Figure 5:
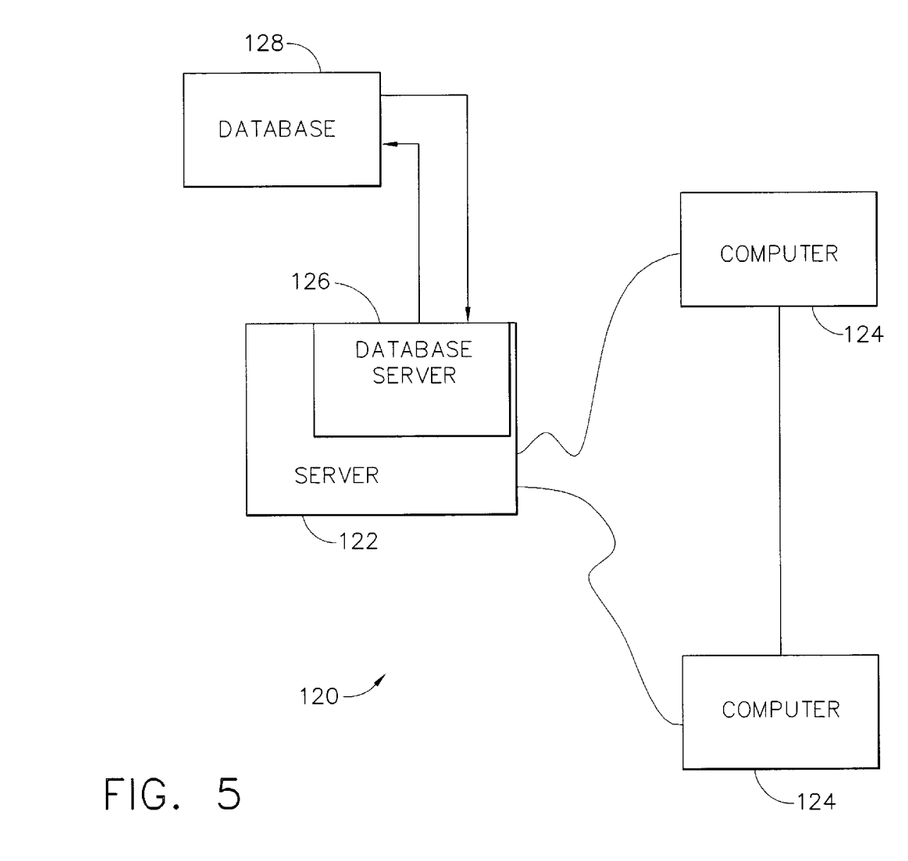
FIG. 5 is a block diagram of a system for determining resilience of spring washers.

FIG. 5 is a block diagram of a system 120 for determining resilience of spring washers. System 120 includes a server 122 and a plurality of devices 124 connected to server 122. In one embodiment, devices 124 are computers including a web browser, and server 122 is accessible to devices 124 via the Internet. In an alternative embodiment, devices 124 are servers for a network of customer devices. System 120 is coupled to a mass storage device (not shown). In the exemplary embodiment, server 122 includes a database server 126 coupled to a centralized database 128.

Devices 124 are interconnected to the Internet through many interfaces including through a network, such as a local area network (LAN) or a wide area network (WAN), through dial-in-connections, cable modems and special high-speed ISDN lines. Alternatively, devices 124 could be any device capable of interconnecting to the Internet including a web-based phone or other web-based connectable equipment. A database providing information relating to the plurality of plants is stored on server 122 and can be accessed by users at one of devices 124 by logging onto server 122 through one of devices 124.

System 120 is configured to provide various user interfaces whereby users enter spring washer data. Server 122 accesses stored information and downloads the requested operational data to at least one of the client systems 124, when the request to download is received from client system 124. The databases are accessed by users using client system 124 configured with a standard web browser.

Figure 6:
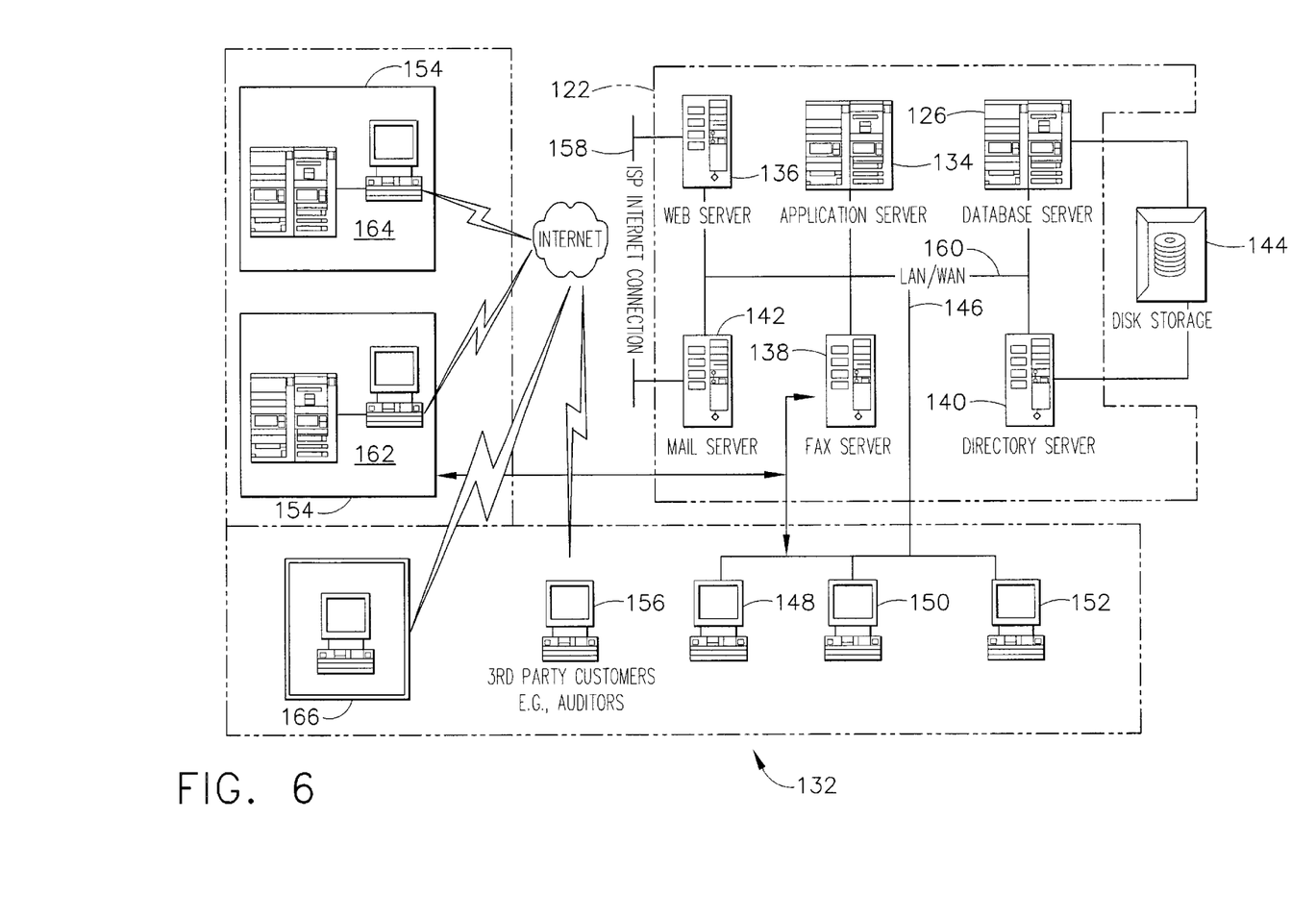
FIG. 6 is an expanded version block diagram of an exemplary embodiment of a server architecture of a system for determining resilience of spring washers.

FIG. 6 is an expanded version block diagram of an exemplary embodiment of a server architecture of a system 132 for determining resilience of spring washers. Components of system 132, identical to components of system 120 (shown in FIG. 1), are identified in FIG. 6 using the same reference numerals as used in FIG. 5. System 132 includes server sub-system 122 and user devices 124. Server sub-system 122 includes database server 126, an application server 134, a web server 136, a fax server 138, a directory server 140, and a mail server 142. A disk storage unit 144 is coupled to database server 126 and directory server 140. Servers 126, 134, 136, 138, 140, and 142 are coupled in a local area network (LAN) 146. In addition, a system administrator workstation 148, a user workstation 150, and a supervisor workstation 152 are coupled to LAN 146. Alternatively, workstations 148, 150, and 152 are coupled to LAN 146 via an Internet link or are connected through an intranet.

Each workstation 148, 150, and 152 is a personal computer having a web browser. Although the functions performed at the workstations typically are illustrated as being performed at respective workstations 148, 150, and 152, such functions can be performed at one of many personal computers coupled to LAN 146. Workstations 148, 150, and 152 are illustrated as being associated with separate functions only to facilitate an understanding of the different types of functions that can be performed by individuals having access to LAN 146.

In another embodiment, server sub-system 122 is configured to be communicatively coupled to various individuals or employees 154 and to users 156 via an ISP Internet connection 158. The communication in the exemplary embodiment is illustrated as being performed via the Internet, however, any other wide area network (WAN) type communication can be utilized in other embodiments, i.e., the systems and processes are not limited to being practiced via the Internet. In addition, and rather than a WAN 160, local area network 146 could be used in place of WAN 160.

In the exemplary embodiment, any authorized individual or an employee of the business entity having a workstation 162 can access server sub-system 122. One of user devices 124 includes a senior manager's workstation 164 located at a remote location. Workstations 162 and 164 are personal computers having a web browser. Also, workstations 162 and 164 are configured to communicate with server sub-system 122. Furthermore, fax server 138 communicates with employees located outside the business entity and any of the remotely located user systems, including a user system 166 via a telephone link. Fax server 138 is configured to communicate with other workstations 148, 150, and 152 as well.

As a load P is applied to contact housing support 82 (shown in FIG. 2), each washer 74 (shown in FIGS. 1, 2, 3, and 4) within series stack 104 (shown in FIG. 4) deflects $X_s$ and each washer within parallel stack 102 (shown in FIG. 4) deflects $X_p$ for a total stack deflection $X_{tot}$. Washers 74 have a plurality of inherent data used in determining resilience, including a dish height h, a thickness t, an outside diameter $d_c$, an inside diameter $d_i$, and a modulus of elasticity $E_w$ equal to $3.0 \times 10^6$ psi. In one embodiment, t is approximately equal 0.291 inches, $d_o$ is approximately equal 4.921 inches, $d_i$ is approximately equal 2.791 inches, h is approximately equal 0.094 inches, and Poisson's ratio $\mu$ is equal 0.3. Furthermore, in the exemplary embodiment, the number of springs in series $n_s$, is ten, the number of springs in parallel $n_p$ is two, and the number of parallel sets in series $n_{s2}$ is fourteen.

It is known to calculate the load P that may be applied to a single spring washer using the equation:

$$P = \frac{Ew \cdot y}{(1-\mu^2) \cdot M \cdot \left(\frac{do}{2}\right)^2} \cdot \left[\left(h - \frac{y}{2}\right) \cdot (h-y) \cdot t + t^3\right] \quad (1)$$

where:

$$M = \frac{6}{\pi \cdot \ln(r)} \left[\frac{R-1}{R}\right]^2; \quad R = \frac{do}{di};$$

and y represents the deflection of a single washer. However, equation (1) is only applicable to a single washer and as such, does not provide the resilience for a stack of washers without including a plurality of assumptions and non-empirical data.

Systems 132 and 120 determine resilience of spring washers based on an energy model, such that total potential energy PE_total is equal to the sum of the individual potential energy of series stack 104, parallel stack 102, hanger rod 70, and beam 68. Mathematically, the total potential energy PE_total is represented by:

$$PE\_total = PE\_series + PE\_parallel + PE\_rod + PE\_beam \quad (2)$$

wherein PE_series represents the work done by springs in series, PE_parallel represents the work done springs in parallel, PE_rod represents the work done by the hanger rod, and PE_beam represents the work done by the beam. In addition, the total applied force is represented by:

$$F := DW + \frac{\pi}{4} \cdot d\_housing^2 \cdot p \quad (3)$$

wherein F represents a total applied force, DW represents the falling weight, d_housing represents the outside diameter of the housing, and p represents the reactor pressure in psi. Because gap 89 is defined, equation (3) is modified to include gap 89, such that work done by a falling weight is represented by:

$$F^*(X_{tot} + d1) \quad (4)$$

in which $X_{tot}$ represents the total deflection of the spring stack including the hanger rod and beam in inches, and d1 represents a width of gap 89.

Using equation (2), the work done by the plurality of springs in the series arrangement is determined using the following equation:

$$PE\_series = \int_0^{Xs} ns \cdot P\_series \, dy \quad (5)$$

which represents the integral of the product of the load and the distance of the series stack. To solve the equation, let C represent the first fraction illustrated in equation (1), i.e., $C = Ew/[(1-\mu^2)*M*(do/2)^2]$, and after substituting for P_series and integrating yields:

$$PE\_series = n_s \cdot C \cdot \left[\frac{1}{8}Xs^4 - \frac{h \cdot t}{2}Xs^3 + \frac{1}{2}(h^2 + t^3) \cdot Xs^2\right] \quad (6)$$

Using equation (2), the work done by the plurality of springs in the parallel arrangement is determined using the following equation:

$$PE\_parallel = \int_0^{Xs} n_{s2} \cdot n_p \frac{P\_series}{n_p} \, dy \quad (7)$$

which represents the integral of the product of the load and the distance of the parallel stack with respect to the series stack. Solving this in a manner similar to that above for the series stack yields:

$$PE\_parallel = n_{s2} \cdot C \cdot \left[\frac{t}{8}Xp^4 - \frac{h \cdot t}{2}Xp^3 + \frac{1}{2}(h^2 + t^3) \cdot Xp^2\right] \quad (8)$$

Thus, $X_{tot} = n_s X_s + n_{s2} X_p$ \quad (9)

Equating potential energies yields a first non-linear equation:

$$F \cdot (Xtot + dl) = n_s \cdot C \cdot \left[ \frac{t}{8} Xs^4 - \frac{h \cdot t}{2} Xs^3 + \frac{1}{2}(h^2 + t^2) \cdot Xs^2 \right] + \text{PE\_parallel} \quad (10)$$

Equation (10) may be solved by using equation (8) to yield:

$$F \cdot (Xtot + dl) = ns \cdot C \cdot \left[ \left(\frac{t}{8}\right) \cdot Xs^4 - \frac{1}{2} \cdot h \cdot t \cdot Xs^3 + \frac{1}{2} \cdot [(h^2) \cdot t + t^3] \cdot Xs^2 \right] + ns2 \cdot C \cdot \left[ \left(\frac{t}{8}\right) \cdot Xp^4 - \frac{1}{2} \cdot h \cdot t \cdot Xp^3 + \frac{1}{2} \cdot [(h^2) \cdot t + t^3] \cdot Xp^2 \right]$$

$X_s$ and $X_p$ may then be related by using the following equation:

$$P\_\text{series} = n_p * P\_\text{parallel} \quad (11)$$

Solving equation (11) yields a second non-linear equation (12):

$$C\left[ \frac{t}{2} Xs^3 - \frac{3}{2} htXs^2 + [(h^2)t + t^3] \cdot Xs \right] = npC \cdot \left[ \frac{t}{2} Xp^3 - \frac{3}{2} htXp^2 + [(h^2)t + t^3] \cdot Xp \right]$$

Accordingly, using equations (5) and (7) in conjunction with equation (2) yields two unknowns, i.e, Xs and Xp, and two non-linear equations, i.e., equations (10) and (12). The only constraint is that the displacement can not be greater than washer height h, and as such, in the exemplary embodiment, Xs and Xp must be between 0.0 and 0.094. In one embodiment, Xs and Xp are solved using a Fortran program. In an alternative embodiment, Xs and Xp are solved using a Mathead program. The impact force of the washers may be easily determined using the solutions for Xs and Xp and the following equations:

Impact force=kstack*Xtot, in which kstack represents the stiffness of the washer stack.

The above-described system and method enables an impact force or resilience of a spring washer shock absorber system. More specifically, the system and method provide a generic analysis of a complex spring washer system using non-linear equations derived using empirical data. As a result, an analytical method is provided which facilitates determining an impact force of spring washer absorber systems in a more accurate and timely manner than is possible using known methods and systems.

While the invention has been described in terms of various specific embodiments, those skilled in the art will recognize that the invention can be practiced with modification within the spirit and scope of the claims.

What is claimed is:

1. A method for determining resilience of a plurality of spring washers stacked in a series arrangement, said method comprising:
   determining the potential energy for the series arrangement by integrating the product of the axial load applied to the series arrangement, the displacement of the series arrangement, and the number of spring washers stacked in the series arrangement; and
   solving at least two non-linear equations to determine the resilience of the spring washers stacked in the series arrangement.

2. A method in accordance with claim 1 wherein solving at least two non-linear equations further comprises determining a stiffness of the series arrangement for a given load.

3. A method in accordance with claim 1 wherein the plurality of spring washers stacked in a series arrangement are stacked in combination with a plurality of spring washers in a parallel arrangement, said solving at least two non-linear equations further comprising determining the potential energy for the spring washers arranged in the parallel arrangement.

4. A method in accordance with claim 3 wherein determining the potential energy for the spring washers arranged in the parallel arrangement further comprises integrating the product of the axial load applied to the parallel arrangement, the displacement of the parallel arrangement, the number of spring washers stacked in the parallel arrangement, and the number of spring washers stacked in the series arrangement.

5. A method in accordance with claim 3 wherein the plurality of spring washers stacked in a series arrangement are stacked in combination with at least one linear spring, said solving at least two non-linear equations further comprising determining the potential energy for the linear spring.

6. A method in accordance with claim 1 wherein the plurality of spring washers stacked in a series arrangement are stacked in combination with at least one linear spring, said solving at least two non-linear equations further comprising determining the potential energy for the linear spring.

7. An apparatus for determining resilience of a plurality of spring washers stacked in a series arrangement, said apparatus comprising a processor programmed to:
   integrate the product of the axial load applied to the series arrangement, the displacement of the series arrangement, and the number of spring washers stacked in the series arrangement to determine the potential energy for the series arrangement; and
   solve at least two non-linear equations to determine the resilience of the spring washers stacked in the series arrangement.

8. An apparatus in accordance with claim 7 wherein said processor further programmed to determine a stiffness of the series arrangement for a given load.

9. An apparatus in accordance with claim 7 wherein said processor further programmed to determine the potential energy of at least one linear spring stacked in combination with the plurality of spring washers stacked in the series arrangement.

10. An apparatus in accordance with claim 7 wherein said processor further programmed to determine the potential energy of at least two spring washers stacked in combination with the plurality of spring washers stacked in the series arrangement.

11. An apparatus in accordance with claim 10 wherein said processor further programmed to integrate the product of the axial load applied to the parallel arrangement, the displacement of the parallel arrangement, the number of spring washers stacked in the parallel arrangement, and the number of spring washers stacked in the series arrangement to determine the potential energy of the at least two spring washers.

12. An apparatus in accordance with claim 10 wherein said processor further programmed to determine the potential energy of at least one linear spring stacked in combination with the plurality of spring washers stacked in the series arrangement and the at least two washers stacked in the parallel arrangement.

13. An apparatus in accordance with claim 12 wherein the spring washers stacked in the series arrangement and the at least two spring washers stacked in the parallel arrangement comprise control rod drive housing support washers, said processor further configured to determine the potential energy of the control rod housing support including at least one hanger rod coupled to the spring washers.

14. A system for determining resilience of a plurality of spring washers stacked in a series arrangement, said system comprising
   a client system comprising a browser;
   a data storage device for storing information relevant to a plurality of users; and
   a server system configured to be coupled to said client system and said data storage device, said server system further configured to integrate the product of the axial load applied to the series arrangement, the displacement of the series arrangement, and the number of spring washers stacked in the series arrangement to determine the potential energy for the series arrangement, and to solve at least two non-linear equations to determine the resilience of the spring washers stacked in the series arrangement.

15. A system in accordance with claim 14 wherein said server system further configured to determine the potential energy of at least one linear spring stacked in combination with the plurality of spring washers stacked in the series arrangement.

16. A system in accordance with claim 15 wherein said server system further configured to determine the potential energy of at least two spring washers stacked in combination with the plurality of spring washers stacked in the series arrangement by integrating the product of the axial load applied to the parallel arrangement, the displacement of the parallel arrangement, the number of spring washers stacked in the parallel arrangement, and the number of spring washers stacked in the series arrangement to determine the potential energy of the at least two spring washers.

17. A system in accordance with claim 14 wherein said server system further configured to determine the potential energy of at least two spring washers stacked in combination with the plurality of spring washers stacked in the series arrangement by integrating the product of the axial load applied to the parallel arrangement, the displacement of the parallel arrangement, the number of spring washers stacked in the parallel arrangement, and the number of spring washers stacked in the series arrangement to determine the potential energy of the at least two spring washers.

* * * * *